(12) United States Patent
McGillin

(10) Patent No.: US 8,392,232 B2
(45) Date of Patent: Mar. 5, 2013

(54) HEALTHCARE RESOURCE MANAGEMENT SYSTEM

(75) Inventor: Madelyn McGillin, Wayne, PA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 1607 days.

(21) Appl. No.: 11/381,479

(22) Filed: May 3, 2006

(65) Prior Publication Data
US 2006/0287906 A1    Dec. 21, 2006

Related U.S. Application Data

(60) Provisional application No. 60/691,223, filed on Jun. 16, 2005.

(51) Int. Cl.
*G06Q 10/00* (2006.01)
(52) U.S. Cl. ........... 705/7.12; 705/2; 705/7.13; 600/300
(58) Field of Classification Search .............. 705/2, 7.12, 705/7.13; 600/300
See application file for complete search history.

(56) References Cited

U.S. PATENT DOCUMENTS

| | | | |
|---|---|---|---|
| 7,657,445 B1 * | 2/2010 | Goux ................................. | 705/3 |
| 2004/0019504 A1 * | 1/2004 | Korom et al. ...................... | 705/2 |
| 2004/0181528 A1 | 9/2004 | Tirinato et al. | |
| 2005/0071190 A1 | 3/2005 | Herger et al. | |
| 2005/0075902 A1 * | 4/2005 | Wager et al. ....................... | 705/2 |
| 2005/0075904 A1 | 4/2005 | Wager et al. | |
| 2005/0137929 A1 * | 6/2005 | Frazier et al. ...................... | 705/9 |
| 2005/0197544 A1 | 9/2005 | Bernstein | |
| 2006/0074740 A1 * | 4/2006 | Garcia et al. ...................... | 705/9 |
| 2006/0111939 A1 * | 5/2006 | Bixler et al. ....................... | 705/2 |
| 2006/0206013 A1 * | 9/2006 | Rothman et al. .............. | 600/300 |

OTHER PUBLICATIONS

RES-Q® Workload and Productivity Management, published Jun. 6, 2004 (retrieved from http://web.archive.org/web/20040606094031/http://www.res-q.com/index_products.html.*
RES-Q® for Windows, Patient Attribute Module, published Jun. 6, 2004 (retrieved from http://web.archive.org/web/20040606094031/http://www.res-q.com/indexproducts.html).*
RES-Q® Labor Resource Management and Employee Scheduling, published Jun. 6, 2004 (retrieved from http://web.archive.org/web/20040606094031/http://www.res-q.com/index_products.html).*
RES-Q® Workload and Productivity Management, published Jun. 6, 2004 (retrieved from http://web.archive.org/web/20040606094031/http://www.res-q.com/index_products.html).*
RES-Q® for Windows, Patient Attribute Module, published Jun. 6, 2004 (retrieved from http://web.archive.org/web/20040606094031/http://www.res-q.com/index_products.html).*

* cited by examiner

*Primary Examiner* — Lynda Jasmin
*Assistant Examiner* — Timothy Padot
(74) *Attorney, Agent, or Firm* — Alexander J Burke

(57) ABSTRACT

A system determines patient acuity information to identify required staff competencies to meet a workload and supports role based reporting, notification, and escalation when acuity nears or reaches a predetermined saturation threshold. A system predicts healthcare worker workload using an acquisition processor to acquire multiple data items associated with care requirements of a particular patient from multiple different sources. A data processor determines an acuity score of the particular patient by determining a single score comprising a combination of weighted individual score values derived from corresponding individual items of the multiple data items. A translation processor interprets determined acuity score to provide an estimated healthcare worker workload for meeting the care requirements of the particular patient by using predetermined translation data associating acuity score with corresponding healthcare worker workload.

21 Claims, 4 Drawing Sheets

| Acuity Scores (203) | Staffing Requirements (205) | Escalation (207) |
|---|---|---|
| 0 – 150 | 1.00 | None |
| 150 – 175 | 1.25 | + 5 Acuity Change |
| 175 – 200 | 1.25 | + 5 Acuity Change |
| 200 – 225 | 1.50 | +10 Acuity Change |
| 225 – 250 | 1.50 | + 20 Acuity Change |
| 250 – 275 | 2.00 | + 20 Acuity Change |
| 275 – 300 | 2.00 | + 20 Acuity Change |
| 300 – 325 | 2.25 | No Escalation |
| 325 – 350 | 2.25 | +5 Acuity Change |
| 350 – 375 | 2.50 | + 5 Acuity Chang |
| 375 – 400 | 2.50 | + 10 Acuity Change |
| 400 – 425 | 3.00 | + 10 Acuity Change |
| 425 – 450 | 3.25 | + 20 Acuity Change |
| 450 – 475 | 3.25 | No Escalation |
| 475 – 500 | 3.50 | + 5 Acuity Change |
| 500 – 525 | 3.50 | +5 Acuity Change |
| 525 – 550 | 4.00 | +10 AcuityChange |
| 550 – 575 | 4.25 | + 10 Acuity Change |
| 575 – 600 | 4.25 | + 20 Acuity Change |
| 600 – 625 | 4.50 | No Escalation |
| 625 – 650 | 4.50 | + 5 Acuity Change |
| 650 – 675 | 5.00 | + 5 Acuity Change |
| 675 – 700 | 5.25 | + 10 Acuity Change |
| 700 – 725 | 5.25 | + 10 Acuty Change |
| 725 – 750 | 5.50 | + 20 Acuity Change |
| 750 – 775 | 5.50 | No Escalation |
| 775 – 800 | 6.00 | + 5 Acuity Change |
| 800 – 825 | 6.25 | + 5 Acuity Change |

HEALTHCARE RESOURCE MANAGEMENT SYSTEM

This is a non provisional application of provisional application Ser. No. 60/691,223 by M. MeGillin. filed Jun. 16, 2005.

FIELD OF THE INVENTION

This invention concerns a system for predicting healthcare worker workload based on acuity scores (e.g., degree of severity) of patient condition for meeting care requirements of patients.

BACKGROUND OF THE INVENTION

The staffing of a patient care area to meet the needs of patients is a complex and challenging problem for healthcare organizations. Patient acuity (severity of patient medical condition) fluctuates substantially throughout a work shift. These fluctuations are unpredictable hampering prediction of staffing needs. It is a common occurrence for hospitals to have at least one nursing unit experiencing a staffing situation in which patient care needs exceed the capacity of the nursing staff. Reserve temporary staff and management staff may be allocated to support these situations, however reserve staff are often allocated late or are available after delay and effectively deliver care after capacity saturation. Such reserve staff are also often unable to provide real assistance. Also nursing staff may be too busy providing care to assess care needs and notify management that additional support is required or to recognize the occurrence of a change in patient acuity. Further, if a nurse does call for assistance, resource allocation managers typically have no quantitative data to support or deny a request. The managers are uncertain if a request is based upon fact or perception and personal bias of a manager or supervisor may impact response to perceived chances in acuity.

Untimely or inadequate response to changes in patient acuity may result in an under performing work environment with patients not getting required care due to healthcare provider delay or omission in administering required patient care. Shortage of nursing staff in some regions exacerbates the problem. In order to address this problem regulatory regimes have been adopted or proposed to require mandatory staffing levels and the use of a system to measure nursing staff required to provide patient care. Although existing acuity systems support financial, budgetary and accreditation requirements, they do not provide management support in responding in real time, to shifts in patient acuity and consequent staffing need changes. A system, according to invention principles, integrated with a healthcare information system addresses these needs and associated problems.

SUMMARY OF THE INVENTION

A system provides real time assessment and management of patient acuity information to identify required care staff (and associated skills) by using data collected from multiple patients to assign a weighted value to a data element that accurately reflects the importance and complexity of each data source in measuring patient acuity. A system predicts healthcare worker workload using an acquisition processor to acquire multiple data items associated with care requirements of a particular patient from multiple different sources. A data processor determines an acuity score of the particular patient by determining a single score comprising a combination of weighted individual score values derived from corresponding individual items of the multiple data items. A translation processor interprets determined acuity score to provide an estimated healthcare worker workload for meeting the care requirements of the particular patient by using predetermined translation data associating acuity score with corresponding healthcare worker workload.

BRIEF DESCRIPTION OF THE DRAWING

FIG. 2 shows a table indicating patient acuity scores and associated staffing requirements and escalation thresholds, according to invention principles.

DETAILED DESCRIPTION OF THE INVENTION

Figure 1:
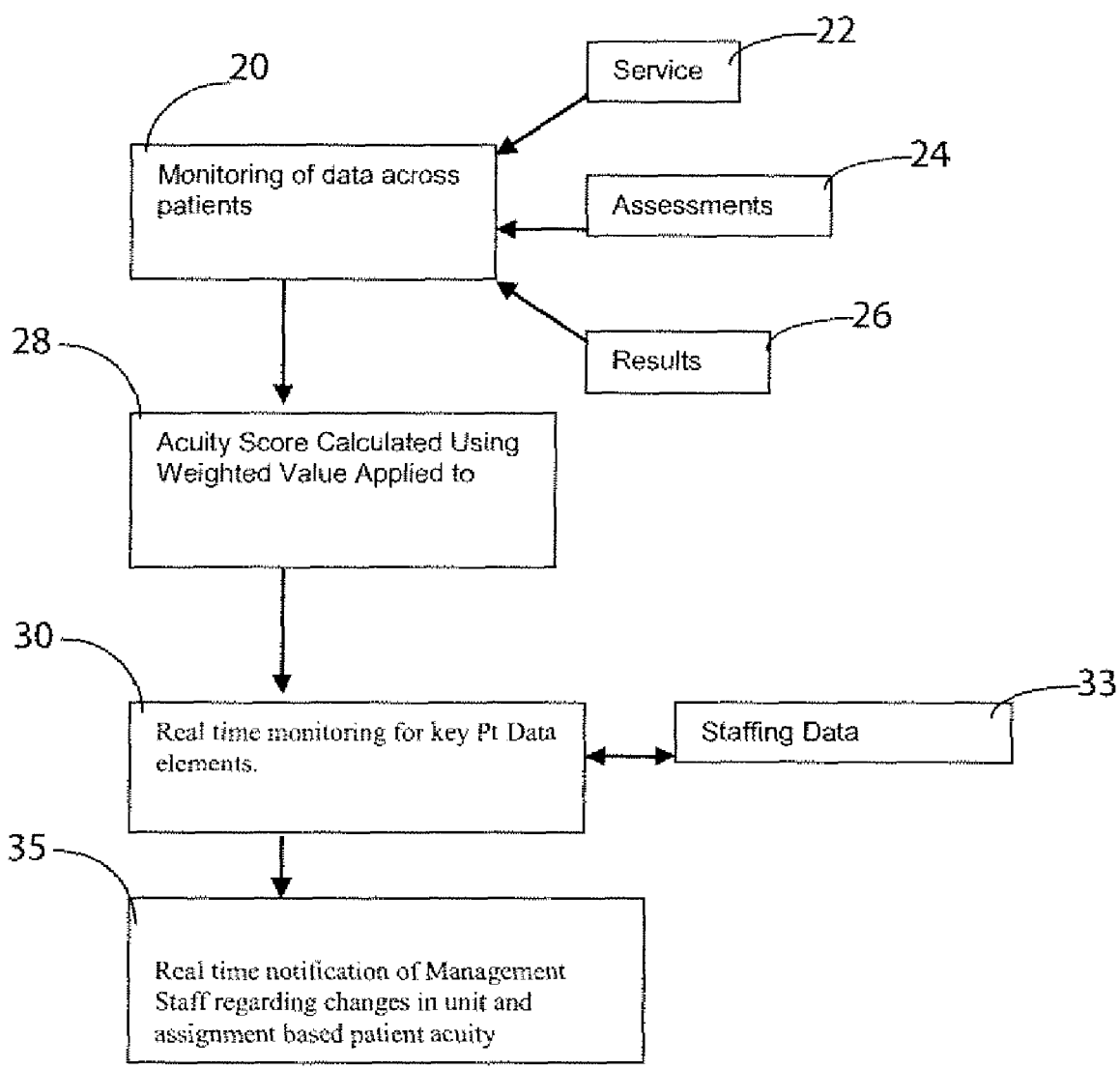
FIG. 1 shows a system for managing healthcare worker workload, according to invention principles.

A system for managing and predicting healthcare worker workload provides real time assessment and management of patient acuity (e.g., severity of patient medical condition) information to identify required care staff (and associated skills). The system uses data collected from multiple patients to assign a weighted value to a data element that accurately reflects the importance and complexity of each data source in measuring patient acuity. The system provides real time notification and response to changes in patient acuity data to facilitate reducing patient morbidity and mortality. In addition, nursing staff are advantageously aware that an objective, data driven system is making staffing decisions, reducing decisions based upon favoritism and subjectivity. The system collects and evaluates data concerning individual patient based nursing assignments, assignments for a group of patients, as well as for staffing of an entire care unit.

An acuity based patient classification system as used herein contains a standardized set of criteria based on scientific data that acts as measurement instrument which predicts registered nursing care requirements for individual patients based on severity of patient's illness, need for specialized equipment and technology, intensity of nursing intervention required, and the complexity of clinical nursing judgment needed to design, implement and evaluate an individual patient's nursing care plan consistent with professional standards of care, details the amount of registered nursing care needed, both in numbers of direct care registered nurses and skill mix of nursing personnel required as a (continuous) daily basis for each patient in a nursing department or unit and as stated in terms that readily can be used and understood by direct care nurses. (From an Act Ensuring Patient Safety, Chapter 11 of the General Laws Section 219, proposed legislation for the Commonwealth of Massachusetts).

Existing acuity measurement systems support prospective (for example every 4 hour) review of workload as well as retrospective workload review using patient assessment information and/or patient specific orders. This information is used by the existing systems to predict staffing needed for the next shift hours and to provide trends for budgetary consideration. In contrast, a system according to invention principles provides real time assessment and management of patient acuity information enabling efficient managing of staffing requirements, especially and addresses the needs of patients with complex and rapidly changing care requirements. Patient acuity information is determined using data obtained from multiple sources, including, patient observations, patient monitoring and treatment devices, results (for example laboratory and radiology results) and services (including a Plan of Care and Clinical Treatment Pathway information). The system also performs surveillance and collects acuity data from multiple different patients and assigns a weighted value to a data element that accurately reflects the importance and complexity of each data source in measuring patient acuity. The system uses the acuity data to identify required staff competencies and support rote based reporting, notification, and escalation when acuity nears or reaches a predetermined saturation threshold. The system advantageously employs either on-site, or remote off-site, management of acuity data.

The healthcare worker workload management system calculates patient acuity information automatically and substantially in real time (without manual intervention and substantial storage delay) using data obtained from the multiple sources. A workflow engine in the system automatically monitors and initiates acquisition of patient data affecting patient acuity. A data processor automatically determines an acuity score of a patient by assigning a weighted value to a data element that accurately reflects the importance and complexity of an individual data source in determining patient acuity. A translation processor interprets determined acuity scores in real time to identify required staff competencies and compare the required staff competencies with an existing available skill mix for an entire care unit and for a singe patient care assignment, for example. The system provides reporting, notification and escalation messages concerning determined acuity information and these functions are configured to be appropriate for a healthcare worker role determined from received user identification information.

An executable application as used herein comprises code or machine readable instruction for implementing predetermined functions including those of an operating system, healthcare information system or other information processing system, for example, in response user command or input. An executable procedure is a segment of code (machine readable instruction), sub-routine, or other distinct section of code or portion of an executable application for performing one or more particular processes and may include performing operations on received input parameters (or in response to received input parameters) and provide resulting output parameters. A processor as used herein is a device and/or set of machine-readable instructions for performing tasks. A processor comprises any one or combination oft hardware, firmware, and/or software. A processor acts upon information by manipulating, analyzing, modifying, converting or transmitting information for use by an executable procedure or an information device, and/or by routing the information to an output device. A processor may use or comprise the capabilities of a controller or microprocessor, for example. A display processor or generator is a known element comprising electronic circuitry or software or a combination of both for generating display images or portions thereof. A user interface comprises one or more display images enabling user interaction with a processor or other device.

FIG. 1 shows a system for managing healthcare worker workload. A data processor monitors and acquires 20 data representing patient clinical activity including assessments 24, results 26, and services provided to the patient and other patient data 22. The data processor applies a weight to the acquired data indicating importance for use in relative weighting the acquired data in calculating 28 patient acuity. The system performs substantially real time monitoring 30 of staffing data 33 and repositories, medical records and transaction messages in deriving patient data for use in determining changes in patient acuity. Nursing assignment data, for example, received from a Clinical Information System, is considered to evaluate a single nurse assignment in addition to assignments of an entire nursing unit. Staffing data, from a Clinical Information System, and from external systems, is employed in calculating patient acuity. The system also provides substantially real time notification 35 of management staff of changes in care unit and assignment based patient acuity. The system for managing healthcare worker workload is applicable to any patient care area within a hospital, e.g., a radiology department. The system adjusts nursing resources according to real time calculations that are based on patient information derived from multiple sources.

Figure 4:
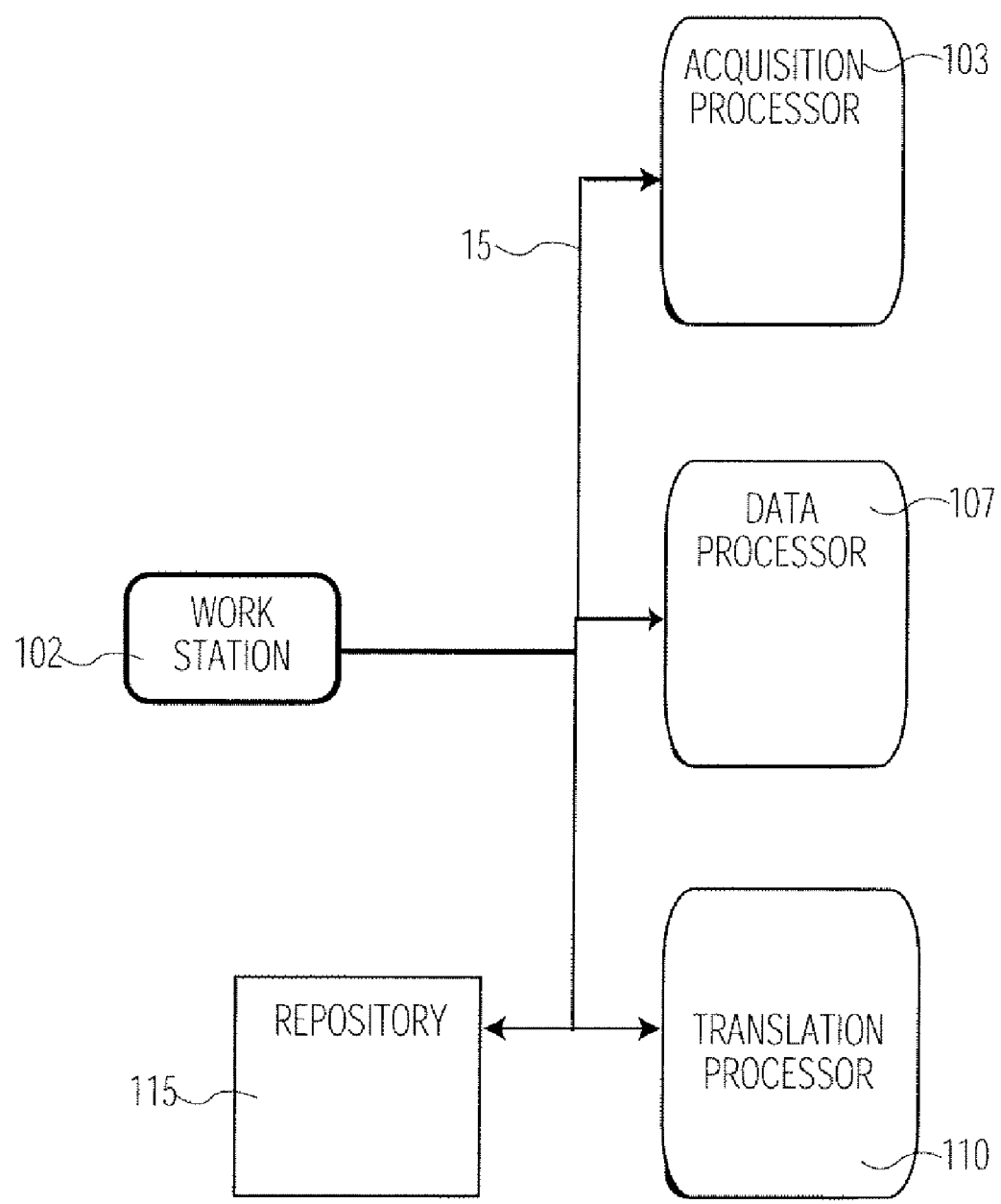
FIG. 4 shows a system for managing healthcare worker workload, according to invention principles.

FIG. 4 shows system 100 for managing healthcare worker workload including acquisition processor 103, data processor 107, translation processor 110 and repository 115 linked by communication path 15 and accessed by a user operating workstation 102. The communication path 15 (otherwise called network, bus, link, connection, channel, etc.) represents any type of protocol or data format. The protocol or data format includes, but is not limited to, one or more of the following: an Internet Protocol (IP), a Transmission Control Protocol Internet protocol (TCPIP), a Hyper Text Transmission Protocol (HTTP), an RS232 protocol, an Ethernet protocol, a Medical Interface Bus (MIB) compatible protocol, a Local Area Network (LAN) protocol, a Wide Area Network (WAN) protocol, a Campus Area Network (CAN) protocol, a Metropolitan Area Network (MAN) protocol, a Home Area Network (HAN) protocol, an Institute Of Electrical And Electronic Engineers (IEEE) bus compatible protocol, a Digital and Imaging Communications (DICOM) protocol, and a Health Level Seven (HL7) protocol.

Acquisition processor 103 acquires multiple data items associated with care requirements of multiple patients including a particular patient from multiple different sources. The data items are acquired as a by-product of a nurse or electronic system entering one or multiple patient assessment findings into a Healthcare Information System (HIS), for example. The acquired data items comprise periodic medical assessments of patient nursing requirements using uniform measurements of patient nursing needs, for example. Data processor 107 determines an acuity score of the particular patient by determining a single score comprising a combination of weighted individual score values derived from corresponding individual items of the acquired multiple data items. Data processor 107 determines an acuity score based on an Assessment Time Factor comprising a numerical sum of assigned values of the patient.

The Assessment Time Factor is a single numerical value representing the amount of nursing activity required to care for the patient or the total workload for the nurse. A nurse selects a response from an electronic assessment form indicating coded findings from a treatment service identification file (a service master file) or similar type of file, comprising a catalog of allowable values organized to support the acuity calculation. A data item has an association to a number that represents a relative work unit (specific task) for the item. The value can be equated to the amount of time required to perform the work unit or to another user defined value that assists nursing personnel, for example, to determine the amount of effort required to do the work unit. A periodic patient assessment (or baseline) may be performed when nursing employees begin a work shift or are changed during a work shilt as required to meet changes associated with patient condition. Medical characteristics or findings used to calculate an Assessment Time Factor include, for example, whether the patient is hard of hearing (HOH), blind, disabled, unconscious, uses a non-native language, patient care preferences, has dignitary status (VIP) and physical disability (ADL).

Figure 3:
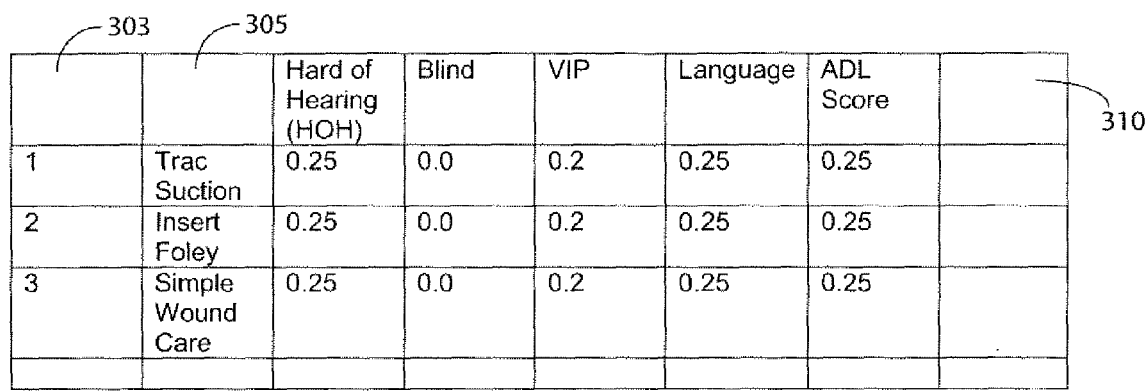
FIG. 3 shows a table indicating intervention time adjustment factors, according to invention principles.

FIG. 3 shows a table indicating intervention time adjustment factors used by data processor 107 in an exemplary determination of an individual acuity score for an individual patient 'P' at time 't' comprising a sum of assessments including routine care needs, interventions and result scores, for example. The table shows intervention time adjustment factors for three types of care procedures (labeled 1, 2 and 3 in column 303) and identified in column 305. The table indicates intervention time adjustment factors for the three types of care procedures for patients having one or more of the characteristics identified in row 310 and comprising being hard of hearing (HOH), being blind, having dignitary status (VIP) and having a physical disability (ADL). Acuity score A for a group of M patients A (P, t) is summed for the M patients, $A(P, t) = \{(\text{Patient Intervention Time} \times \text{Intervention Assessment Time Factor})\} + \{(\text{Patient's Routine Care time} \times \text{Routine Care Assessment Time Factor})\} + \{(\text{Patient Results} \times \text{Results Assessment Factor})\}.$ Specifically, $$A(P,t) = \sum_{\text{patient } i=1}^{i=M} (PIT_i \times IATF) + (PRCT_i \times RCATF) + (PR_i \times RAF)$$

For example a patient having characteristics [blind][VIP][HOH] has an intervention tiMe adjustment factor of, $0 + 0.2 + 0.25 = 0.45$ The Intervention assessment factor of a normal patient=1.0. Therefore, for a patient having characteristics [blind][VIP][HOH], a predetermined Patient Intervention Time for a healthcare worker to perform tracheal treatment procedure 1 of FIG. 3 (tracheal suctioning) is adjusted (increased) by an Intervention Assessment Time Factor of 1.0+0.45=1.45. In a similar manner, a Patient's Routine Care time is adjusted by a Routine Care Assessment Time Factor and Patient Results assessment time is adjusted by a Results Assessment Factor. Thereby data processor 107 determines a single acuity score of multiple patients by determining for individual patients, a single score comprising a combination of weighted individual score values derived from corresponding individual items of multiple acquired data items and by combining the determined single scores for multiple patients to provide the single acuity score.

Translation processor 110 interprets the determined acuity score to provide an estimated healthcare worker workload for meeting the care requirements of multiple patients including the particular patient by using predetermined translation data associating acuity score with corresponding healthcare worker workload. Translation processor 110 interprets a determined acuity score to provide an estimated nursing workload, for example, by comparing the estimated healthcare worker workload with available worker resources.

Patient acuity scores are translated to identify a total workload for a nurse, at time 't', and includes the interventions, routine care and result data assessment tasks performed by a nurse, for example. A hospital determines staffing required based on multiple patient acuity scores. Data processor 107 determines acuity changes, up or down, for individual patients within a nursing care unit and an average acuity score per individual patient (e.g., score=25). Translation processor 110 compares an individual patient acuity score with a predetermined threshold and also compares an average (mean, median, other) patient acuity score of multiple patients of a care unit, for example, with a predetermined threshold. The threshold indicates an escalation and alert point used for initiating generation an alert message to a supervisor to prompt adding staff, or to a workflow engine for automatically allocating staff and changing or allocating task assignments. The alert message may also request a supervisor, for example, to review the workload situation.

Table 1 illustrates actions triggered based on acuity score changes acquired in real time for individual patients. For an increase in patient acuity score value (since a last baseline measurement) of less than an escalation threshold of five, no action is taken and for an increase in patient acuity score value of five or more, translation processor 110 alerts a supervisor of the situation. The escalation threshold is set at +5 from a baseline acuity score value.

Patient 1 score 25+10=35
Patient 2 score 32−6=26
Patient 3 score 27+7=34
Patient 4 score 19−4=15
Patient 5 score 21−2=19

Table 1. Patient Acuity Change Escalation

A nursing supervisor is notified via pager (or other mobile or communication device) of the acuity score increase for patients 1 and 3 exceeding or equaling the +5 threshold increase value.

FIG. 2 shows a table indicating patient acuity scores and associated staffing requirements and escalation thresholds for a forty bed medical unit (e.g., a nursing care unit). Column 203 indicates acuity score ranges for the occupants of the medical unit, column 205 indicates corresponding staffing requirements and column 207 identifies associated escalation thresholds. Row 210 indicates for a patient acuity score range of 0-150, a single nurse is sufficient and an increase in acuity value within this range does not trigger alert escalation. Row 213 indicates for a patient acuity score range of 275-300, two nurses are required and an increase in acuity value within this range of +20 or more, initiates translation processor 110 to generate an alert message to notify a supervisor of the acuity score increase. Row 217 indicates a patient acuity score range of 300-325 needs the allocation of the equivalent of 2.25 nursing staff and an increase in acuity value within this range does not trigger alert escalation.

System 100 (FIG. 1) automatically monitors patient data to identify critical or abnormal results such as laboratory and radiology results. Critical results predict changes in patient medical condition requiring additional care needs and are allocated a score by data processor 107 which is added to the total acuity score for the patient. New orders for treatment for a patient during a nursing shift also change patient acuity score. Clinicians periodically assess patient progress and initiate diagnostic or therapeutic treatment orders for patients. An individual treatment order may have an associated relative value work unit that automatically contributes to the acuity score determined by data processor 107 as a result of placing the order. New treatment orders may require nursing intervention to complete the orders. Treatment orders requiring nursing intervention are weighted by data processor 107 in calculating an acuity score using the patient's Assessment Time Factor. In response to a treatment order being entered into a computerized order entry system, for example, data processor 107 calculates a patient acuity score change by adding the acuity value associated with the order weighted using the Patient Assessment Time Factor, to the patient's aggregated acuity score. Treatment orders may include treatments, medications, and associated patient education including discharge instructions.

Routine care given to a patient in the hospital includes assistance with activities of daily living including bathing and toileting. Data processor 107 determines an acuity change associated with a routine care treatment protocol by adding the routine care treatment acuity value weighted using the Patient Assessment Time Factor, to the patient's aggretgated acuity score. Adverse events also may modify patient condition and increase patient acuity score. Adverse events include patient falls or accidents, medication errors, medical emergency (e.g., myocardial infarctions (MI), acute respiratory distress), medication allergies, or other adverse medical events. Adverse events require nursing intervention and change patient acuity values and are identified by patient monitors that track patient vital signs and ability to breathe, for example. The monitoring devices trigger alerts that warn of changes in the patient condition and are connected to a hospital information system enabling coded information to trigger alerts for nursing intervention to address the patient condition. Data processor 107 automatically determines when adverse events exceed predetermined thresholds, acquires resulting changed acuity values and initiates performance of a computation of patient acuity score.

In system 100 (FIG. 4), acquisition processor 103 acquires multiple data items associated with care requirements of a particular patient (or multiple patients in another embodiment) from multiple different sources. The multiple data items derived from the multiple different sources comprise at least two of, patient medical parameters, patient observations recorded by a healthcare worker, test results for a patient, data recorded in a patient treatment or care plan and medication orders entered for administration to a patient. The multiple data items derived from the multiple different sources may also comprise at least two patient medical parameters of, (a) a blood pressure parameter, (b) a ventilation parameter, (c) a vital sign parameter, (d) a blood oxygen concentration representative parameter, (e) a spontaneous tidal volume parameter, (f) a respiratory rate parameter, (g) a positive end-expiratory pressure parameter, (h) a temperature, (i) a heart rate, (i) a cardiac output, (k) an infusion pump parameter associated with fluid delivery and (l) a drip medication related parameter.

Data processor 107 determines an acuity score of the particular patient (or multiple patients in another embodiment) by determining a single score comprising a combination of weighted individual score values comprising weighted assessments of times involved in caring for a patient and derived from corresponding individual items of the acquired multiple data items. Data processor 107 combines determined single scores of individual patients of multiple patients to provide a single acuity score for multiple patients in another embodiment. Data processor 107 combines the determined single scores for the multiple patients to provide the single acuity score by determining one or more of, a mean score, an average score or a score variance from a mean. The assessments of times involved in caring for a patient comprise times associated with two or more of, intervention, routine care and review of results. The weighted individual score values are derived by weighting corresponding individual items of the acquired multiple data items with a patient assessment time factor determined from medical and non-medical characteristics of a patient. Data processor 107 in one embodiment, weights individual score values according to estimated importance in determining patient care requirements. The medical and non-medical characteristics comprise at least two of, (a) whether the patient is hard of hearing, (b) blind, (c) disabled, (d) unconscious, (e) has a non-native language, (f) patient care preferences, (g) has dignitary status and (h) a physical disability. In one embodiment acquisition processor 103 acquires the individual score values derived from corresponding individual items of the acquired multiple data items.

Data processor 107 also determines a change in acuity score of the particular patient by comparing an acuity score with a previously determined acuity score of the particular patient. Translation processor 110 compares the change in acuity score to a predetermined change threshold and initiates an action (e.g., notification of a supervisory nursing manager) in response to the change in acuity score exceeding the threshold.

Translation processor 110 interprets the determined acuity score to provide an estimated healthcare worker workload for meeting the care requirements of the particular patient (or multiple patients in another embodiment) by using predetermined translation data (e.g., as illustrated in FIG. 2) associating acuity score with corresponding healthcare worker workload. Translation processor 110 compares the estimated healthcare worker workload with available worker resources. The available worker resources are determined based on a determination of an amount of work capable of being done by available workers. The amount of work capable of being done is derived based on factors including, an individual worker skill classification, individual worker experience and worker medical specialty.

Translation processor 110 interprets the determined acuity score to provide an estimated nursing workload. An alert generator in processor 110 automatically initiates generation of an alert message to a supervisory healthcare worker in response to an estimated healthcare worker workload exceeding available worker resources.

Adverse events concerning medication management of Intra Venous (IV) administered drugs similarly may change patient acuity score. In the event of an adverse event, an IV system incorporating parameter monitoring functions connected to system 100 alerts nursing personnel of a need for acute patient support. The alert may include a treatment order to automatically increase patient acuity score corresponding to an associated amount of nursing intervention derived using a menu of items included in a catalog of allowable orders. Data processor 107 continuously computes and displays patient acuity score on workstation 102 using a user configurable presentation employing graphs, such as bar and pie charts, that depict how much nursing care is required to meet patient needs. The graphic presentation may be color coded so that predetermined thresholds are identified indicating when various notification messages are communicated to personnel or functions, e.g., to a workflow engine. In an operation example, a nurse manager receives a pager alert that an individual patient acuity score has exceeded a threshold and the nurse manager initiates escalation steps to increase nursing resources to meet the patient's changed condition.

Data processor 107, in one embodiment, combines scores of patients located at a user defined geographic location, such as a nursing station, nursing unit, ward, or similarly defined unit where multiple patients are attended to by nursing personnel. The geographic locations may be organized by type of patient, such medical, surgical, intensive care (ICU, CCU, SICU), telemetry, pediatric, nursery, neonatal ICU, and psychiatric. Some locations can have more intensive nursing requirements, involving isolation of a patient because of infectious disease or suppressed immune systems. Data processor 107 provides an aggregated acuity score for the patients occupying a defined geographic location (e.g., a healthcare enterprise location) so that the total acuity score value for the location is known. The aggregated acuity score of a geographic location may be presented in a user selectable graphical chart format indicating the total amount of patient acuity for a particular location.

In allocating resources to address an increase in patient acuity score, system 100 employs commonly known nursing skill categories (aide, LPN, RN, BSN, MSN, Clinical Specialist, etc.), specialty categories (critical care, trauma, emergency department, operating room, oncology, pediatrics, rehabilitation, etc) and experience (under 1 year, less than 2, more than 5, more than 10, supervisory, expert clinical specialist). System 100 supports user configuration of other personnel characteristics. System 100 employs a table including nursing skill classification definitions that relate the nursing resources to an amount of work capable of being done, in terms of patient-related and non-patient related work. Patient-related work is defined as direct patient contact handling patient treatment orders indicated in a service master file, for example. Non-patient related work includes, but is not limited to administrative tasks, such as in-service training, routine breaks, meals, and other miscellaneous time categories.

In one embodiment, nursing resources assigned to a user-defined location, such as a nurse station, are aggregated by system 100 to provide a resource indicator. The resource indicator is derived using a denominator value and a nominator value. The numerator value (the sum of acuity scores of patients associated with a particular geographic location) is divided by the denominator value (the amount of nursing resources available to meet patient needs). The resulting resource indicator value indicates resources needed to support the patients at that particular location. If the indicator value indicates resource needs exceed the available resources, system 100 alerts various managers, identified in response to user entered configuration information, using pagers, PDA alerts, cell phones, or similar types of devices, that a location has a short fall of nursing resources, for example. Thereby, management is able to take action to reduce or eliminate the short fall by assigning temporary nursing personnel or initiating similar resource management actions to assist with the increased acuity requirements.

System 100 monitors a trend of both patient acuity and associated nursing resource requirements during various time periods (a shift, a day, a week, a pay-period, a month, a quarter, a year) to predict utilization requirements for budgeting and other managerial work. In an example, a nurse is assigned to care for six patients on a telemetry (wireless) monitoring equipped hospital floor. The six patients range in age from 48 to 90 and have a mixture of diagnoses. The nursing activities and the care given to each patient are determined by clinical treatment pathways ordered for each patient. The nurse enters patient assessment data into a Clinical Information System, which classifies and quantifies the level of care required by individual patients and provides corresponding Assessment Time Factors. Concurrently, system 100 monitors treatment order and result data and uses this data in conjunction with Assessment Time Factors in calculating patient acuity score. The system monitors for changes (increases or decreases) in acuity score and compares the changes to established staffing thresholds for an individual nurse or for a group of nurses.

In the example, the nurse is electronically notified by a bed fall alarm system that one of the patients assigned to the nurse falls out of bed. The nurse is also electronically notified that a second patient develops a dangerous cardiac arrhythmia and hypotension. The nurse performs an assessment of both patients and notifies a physician of the patient change in condition. The physician remotely views patient data and enters treatment orders to institute emergency interventions. A supervisor is alerted since the nurse patient acuity threshold is exceeded. The nurse threshold identifies a workload at which a nurse is unable to manage alone without assistance (e.g., Table 1). System 100 enables the nursing supervisor to look at multiple nursing units to identify nursing areas able to release staff to assist in managing the increase in the patient acuity. System 100 performs and displays calculations that support patient acuity changes and saves calculation data in repository 115 for trend analysis and correlation with standards recommended by professional organizations, or as required to meet statutory laws, such as patient safety.

The systems and processes presented in FIGS. 1-4 are not exclusive. Other systems and processes may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention A system according to invention principles is usable wherever prediction of worker workload is desired. Further, any of the functions provided systems and processes of FIGS. 1-4 may be implemented in hardware, software or a combination of both and may reside on one or more processing devices located at any location of a network linking the FIG. 4 elements or another linked network including another intranet or the Internet.

What is claimed is:

1. A system for predicting healthcare worker workload, comprising:
    at least one processing device operating in response to machine readable instructions and including,
        an acquisition processor for acquiring a plurality of data items associated with care requirements of a particular patient from a plurality of different sources;
        a data processor for determining an acuity score of said particular patient as a summation of time score values of healthcare worker performed different task types, said task types being individually differently weighted by time score adjustment values by determining a single score comprising a summation of at least two of,
            (a) intervention time score values weighted by an intervention time adjustment factor,
            (b) routine care time score values weighted by a routine care time adjustment factor and
            (c) a results assessment time score value weighted by a results assessment time adjustment factor, derived from corresponding individual items of said acquired plurality of data items; and
        a translation processor for,
            comparing the determined acuity score with a previously determined acuity score of said particular patient and initiating a worker notification in response to a change in acuity score exceeding a predetermined threshold and
            interpreting said determined acuity score to provide an estimated healthcare worker workload for meeting said care requirements of said particular patient by using predetermined translation data associating acuity score with corresponding healthcare worker workload.

2. A system according to claim 1, wherein
    said data processor automatically monitors patient data to identify an abnormal laboratory test result exceeding a predetermined threshold and in response, initiates performance of a computation of patient acuity score and said data processor determines an acuity score for a group of patients by summing, (intervention time score values weighted by an intervention time adjustment factor) and (routine care time score values weighted by a routine care time adjustment factor) and (a results assessment time score value weighted by a results assessment time adjustment factor).

3. A system according to claim 2, wherein
said translation processor interprets said determined acuity score to identify required staff competencies and compare the required staff competencies with an existing available skill mix for a singe patient care assignment.

4. A system according to claim 1, wherein
said translation processor compares a change in an acuity score derived for a plurality of patients to a predetermined change threshold and initiates addition of worker support in meeting said care requirements in response to said change in acuity score exceeding said threshold,
said predetermined change threshold is variable based on both said acuity score derived for said plurality of patients and staffing requirements and
said plurality of data items derived from said plurality of different sources comprise at least two of, (a) patient medical parameters, (b) patient observations recorded by a healthcare worker, (c) test results for a patient, (d) data recorded in a patient treatment or care plan and (e) medication orders entered for administration to a patient.

5. A system according to claim 1, wherein
said data processor determines an acuity score A for a group of M patients by summing for the M patients, {(Patient Intervention Time×Intervention Assessment Time Factor)+(Patient's Routine Care time×Routine Care Assessment Time Factor)+(Patient Results×Results Assessment Factor)}.

6. A system according to claim 5, wherein
said single score comprises a combination of weighted individual score values comprising weighted assessments of times involved in caring for a patient and said assessments of times involved in caring for a patient comprise times associated with review of results and A for a group of M patients is A (P, t) where $$A(P,t)=\Sigma(PIT_i \times IATF)+(PRCT_i \times RCATF)+(PR_i \times RAF).$$

7. A system according to claim 1, wherein
said weighted individual score values are derived by weighting corresponding individual items of said acquired plurality of data items with a patient assessment time factor determined from medical characteristics of a patient.

8. A system according to claim 7, wherein
said weighted individual score values are derived by weighting corresponding individual items of said acquired plurality of data items with a patient assessment time factor determined from non-medical characteristics of a patient.

9. A system according to claim 8, wherein
said medical and non-medical characteristics comprise at least two of, (a) whether the patient is hard of hearing, (b) blind, (c) disabled, (d) unconscious, (e) has a non-native language, (f) patient care preferences, (g) has dignitary status and (h) a physical disability.

10. A system according to claim 1, wherein
said plurality of data items derived from said plurality of different sources comprise at least two patient medical parameters of, (a) a blood pressure parameter, (b) a ventilation parameter, (c) a vital sign parameter, (d) a blood oxygen concentration representative parameter, (e) a spontaneous tidal volume parameter, (f) a respiratory rate parameter, (g) a positive end-expiratory pressure parameter, (h) a temperature, (i) a heart rate, (i) a cardiac output, (k) an infusion pump parameter associated with fluid delivery and (l) a drip medication related parameter.

11. A system according to claim 1, including
an alert generator for automatically initiating generation of an alert message to a supervisory healthcare worker in response to an estimated healthcare worker workload exceeding available worker resources, said workload being determined using the single score value.

12. A system according to claim 1, wherein
said translation processor compares said estimated healthcare worker workload with available worker resources.

13. A system according to claim 12, wherein
said available worker resources are determined based on a determination of an amount of work capable of being done by available workers, said amount of work capable of being done is derived based on one or more factors of, (a) an individual worker skill classification, (b) individual worker experience and (c) worker medical specialty.

14. A system according to claim 1, wherein
said translation processor interprets said determined acuity score to provide an estimated nursing workload.

15. A system according to claim 1, wherein
said data processor weights individual score values according to estimated importance in determining patient care requirements.

16. A system according to claim 1, wherein
said acquisition processor acquires said individual score values derived from corresponding individual items of said acquired plurality of data items.

17. A system for predicting healthcare worker workload, comprising:
at least one processing device operating in response to machine readable instructions and including,
an acquisition processor for acquiring a plurality of data items associated with care requirements of a plurality of patients from a plurality of different sources;
a data processor for determining a single acuity score of a plurality of patients by determining for individual patients, a single score comprising a summation of time score values of healthcare worker performed different task types, said task types being individually differently weighted by time score adjustment values comprising a summation of,
(a) intervention score values weighted by an intervention adjustment factor,
(b) routine care score values weighted by a routine care adjustment factor and
(c) a results assessment time score value weighted by a results assessment time adjustment factor, derived from corresponding individual items of said acquired plurality of data items and combining said determined single scores for said plurality of patients to provide said single acuity score; and
a translation processor for,
comparing the determined single acuity score with a previously determined acuity score of said particular patient and initiating a worker notification in response to a change in acuity score exceeding a predetermined threshold and
interpreting said determined single acuity score to provide an estimated healthcare worker workload for meeting said care requirements of said plurality of patients by using predetermined translation data associating acuity score with corresponding healthcare worker workload.

18. A system according to claim 17, wherein
said data processor combines said determined single scores for said plurality of patients to provide said single acuity score by determining at least one of, (a) a mean score, (b) an average score and (c) a score variance from a mean and
automatically monitors patient data to identify an abnormal laboratory test result exceeding a predetermined threshold and in response, initiates performance of a computation of patient acuity score.

19. A system for predicting healthcare worker workload, comprising:
at least one processing device operating in response to machine readable instructions and including,
an acquisition processor for acquiring a plurality of data items indicating assessments of times involved in caring for a patient;
a data processor for determining an acuity score of a particular patient as a summation of time score values of healthcare worker performed different task types, said task types being individually differently weighted by time score adjustment values comprising a summation of,
(a) patient intervention time score value weighted by an intervention assessment time adjustment factor,
(b) routine care time score value weighted by a routine care assessment time adjustment factor and
(c) a results assessment time score value weighted by a results assessment time adjustment factor; and
a translation processor for,
comparing the determined acuity score with a previously determined acuity score of said particular patient and initiating a worker notification in response to a change in acuity score exceeding a predetermined threshold and
interpreting said determined acuity score to provide an estimated healthcare worker workload for meeting said care requirements of said particular patient by using predetermined translation data associating acuity score with corresponding healthcare worker workload.

20. A system according to claim 19, wherein
said weighted assessments of times involved in caring for a patient comprise individual assessments of times involved in caring for a patient weighted with a patient assessment time factor determined from medical, functional and personal characteristics of a patient and
said data processor automatically monitors patient data to identify an abnormal laboratory test result exceeding a predetermined threshold and in response, initiates performance of a computation of patient acuity score.

21. A system for predicting healthcare worker workload, comprising:
at least one processing device operating in response to machine readable instructions and including,
an acquisition processor for acquiring a plurality of data items associated with care requirements of a particular patient from a plurality of different sources;
a data processor for determining a change in acuity score of said particular patient by comparing an acuity score with a previously determined acuity score of said particular patient and initiating a worker notification in response to a change in acuity score exceeding a predetermined threshold, said acuity score comprising a summation of time score values of different task types, said task types being individually differently weighted by time score adjustment values derived from corresponding individual items of said acquired plurality of data items and said data processor automatically monitors patient data to identify an abnormal laboratory test result exceeding a predetermined threshold and in response, initiates performance of a computation of patient acuity score; and
a translation processor for comparing said change in acuity score to a predetermined change threshold and initiating an action in response to said change in acuity score exceeding said threshold.

* * * * *